US006710126B1

(12) United States Patent
Hirt et al.

(10) Patent No.: US 6,710,126 B1
(45) Date of Patent: Mar. 23, 2004

(54) DEGRADABLE POLY(VINYL ALCOHOL) HYDROGELS

(75) Inventors: Thomas Hirt, Rebstein (CH); Troy Holland, Suwanee, GA (US); Vimala Francis, Suwanee, GA (US); Hassan Chaouk, Atlanta, GA (US)

(73) Assignee: Bio Cure, Inc., Norcross, GA (US)

( * ) Notice: Subject to any disclaimer, the term of this patent is extended or adjusted under 35 U.S.C. 154(b) by 149 days.

(21) Appl. No.: 09/714,700

(22) Filed: Nov. 15, 2000

Related U.S. Application Data
(60) Provisional application No. 60/165,531, filed on Nov. 15, 1999.

(51) Int. Cl.⁷ .................................................. C08F 8/00
(52) U.S. Cl. .............................. 525/61; 525/59; 525/50; 525/56
(58) Field of Search .............................. 525/50, 56, 59, 525/61

(56) References Cited

U.S. PATENT DOCUMENTS

| 4,665,123 | A | | 5/1987 | Goldenberg |
| 4,670,506 | A | * | 6/1987 | Goldenberg et al. .......... 525/59 |
| 4,978,713 | A | | 12/1990 | Goldenberg |
| 5,508,317 | A | | 4/1996 | Muller et al. |
| 5,665,840 | A | | 9/1997 | Pohlmann et al. |
| 5,854,382 | A | | 12/1998 | Loomis |
| 5,916,585 | A | * | 6/1999 | Cook et al. ................. 424/426 |
| 5,939,489 | A | * | 8/1999 | Muller ......................... 525/61 |
| 6,011,077 | A | | 1/2000 | Muller et al. |
| 6,271,278 | B1 | * | 8/2001 | Park et al. ................... 521/150 |
| 6,514,535 | B2 | * | 2/2003 | Marchant ..................... 424/486 |

FOREIGN PATENT DOCUMENTS

| EP | 497 611 | 1/1992 | |
| EP | 529 910 | 8/1992 | |
| EP | 529910 A1 | * 3/1993 | ............. C08F/8/00 |
| WO | WO 93/17669 | 9/1963 | |
| WO | WO 96/24073 | 8/1996 | |
| WO | WO 96/24074 | 8/1996 | |
| WO | WO 96/24075 | 8/1996 | |
| WO | WO 97/05185 | 2/1997 | |
| WO | WO 98/12243 | 3/1998 | |
| WO | WO 99/03454 | 1/1999 | |

OTHER PUBLICATIONS

Arshady, R. Polymers for Adv. Technologies, Dec. 1990.

* cited by examiner

Primary Examiner—David W. Wu
Assistant Examiner—Henry Hu
(74) Attorney, Agent, or Firm—Collen A. Beard

(57) ABSTRACT

Biodegradable biocompatible hydrogels based on poly(vinyl alcohol) and methods for their preparation. The methods for preparation of the hydrogels involve the use of prepolymers. The prepolymers have a PVA backbone and pendant chains that include a polymerizable group. In one embodiment, the pendant chains also include a biodegradable region. In another embodiment, biodegradable regions are incorporated into the hydrogel during its formation.

6 Claims, 3 Drawing Sheets

DEGRADABLE POLY(VINYL ALCOHOL) HYDROGELS

RELATED APPLICATIONS

This application claims priority to U.S. Ser. No. 60/165,531, filed on Nov. 15, 1999.

FIELD OF THE INVENTION

The present invention relates generally to degradable hydrogels and more specifically to degradable poly(vinyl alcohol) (PVA) hydrogels that are suitable for use as biomaterials.

BACKGROUND OF THE INVENTION

Biocompatible hydrogels have become a favored material for many biomedical applications. In many cases, it is preferable to employ a hydrogel that is biodegradable so that the body can rid itself of the foreign material over a period of time. One biodegradable hydrogel is disclosed in U.S. Pat. No. 5,410,016 to Hubbell et al. This material is made from biodegradable, polymerizable macromers having a water soluble region, at least one degradable region which is hydrolyzable under in vivo conditions, and free radical polymerizable end groups having the capacity to form additional covalent bonds resulting in macromer interlinking, wherein the polymerizable end groups are separated from each other by at least one degradable region. In preferred embodiments, the macromers include a central backbone of polyethylene glycol flanked by degradable regions of polycaprolactone or polylactide, which are in turn flanked by polymerizable vinyl groups.

A primary disadvantage of the macromers and hydrogels disclosed by Hubbell is that they are inflexible in design. PEG has only two groups which are easily modified, the terminal hydroxyl groups, and those groups are modified with the biodegradable and polymerizable groups. Moreover, Hubbell does not disclose any ways in which the macromers can be modified or in which the hydrogel can be modified after its formation. Also, the degradable PEG material developed by Hubbell et al. exhibits a large degree of swelling in aqueous solutions, which is disadvantageous in many applications.

PVA based hydrogels are disclosed in U.S. Pat. Nos. 5,508,317 and 5,932,674 to Muller. However, these hydrogels are not degradable.

PVA hydrogels offer many advantages over PEG based hydrogels. For example, the availability of pendant OH groups along a PVA backbone adds versatility in terms of the various modifications that could be made to the macromer (e.g. attachment of degradable segments, active agents, hydrophobic groups, etc).

Moreover, a PVA system with its pendant OH groups allows for variations in loading (density) of the attached groups, and this is an important feature to have in a macromer. Third, PEG hydrogels are noted for their superior swelling in aqueous environments. This swelling property could be undesirable for certain applications. With a PVA hydrogel, the choice of a suitable PVA (with appropriate attached groups if desired) can yield a non-swellable, minimally swellable, or even shrinkable system.

Fourth, PVA possesses greater adhesive properties than PEG. This might be desirable for certain applications. Furthermore, PVA due to its hydrocarbon backbone has greater oxidative stability than PEG and it can be stored as aqueous solutions as opposed to PEG that has to be stored as a freeze-dried powder.

Lastly, the preparation of a PVA macromer can be done in aqueous medium with a final ultrafiltration step for purification. As opposed to this, PEG-based acrylates/methacrylates are prepared in organic solvents, and if not purified well can have toxic residuals such as triethylamine hydrochloride.

A disadvantage of the PVA hydrogels that have been developed is that they are not degradable. Accordingly, it would be advantageous to have a PVA hydrogel that is degradable and methods for making such hydrogels. Moreover, it would be advantageous to have a degradable hydrogel having multiple pendant groups that allow for the attachment of various modifiers.

SUMMARY OF THE INVENTION

The invention is directed to biodegradable biocompatible hydrogels based on poly(vinyl alcohol) and methods for their preparation. The degradable hydrogels can be formed in vivo or ex vivo. The hydrogels can be used for a number of biomedical applications, including, but not limited to, implants, embolic agents, wound healing dressings, adhesion prevention, sealants, bulking agents, coatings for biomaterials, and delivery of biologically active compounds such as drugs, genes, proteins, and enzymes. The hydrogels are advantageous in that the PVA backbone can be easily modified and can provide hydrogels having very different properties.

The methods for preparation of the hydrogels involve the use of prepolymers. The prepolymers have a PVA backbone and pendant chains that include a polymerizable group. In one embodiment, the pendant chains also include a biodegradable region. In another embodiment, biodegradable regions are incorporated into the hydrogel during its formation.

In a first general embodiment, a PVA prepolymer having crosslinkable groups and a second component having a degradable region flanked by crosslinkable groups are combined under conditions suitable for crosslinking the groups. The resulting hydrogel that is formed contains PVA chains linked by degradable regions.

In a second general embodiment, PVA prepolymers are formed having pendant crosslinkable groups separated from the PVA backbone by a biodegradable region. Hydrogels are formed by exposing the prepolymers to conditions that initiate crosslinking of the crosslinkable groups.

The many pendant hydroxyl groups of PVA allow great versatility in design of hydrogels with desired characteristics. Suitable hydrogels can be formed without having to employ each of the hydroxyl groups for attaching crosslinkable groups. Certain hydroxyl groups can be modified before the prepolymer is formed, after the prepolymer is formed, or even after the hydrogel is formed.

DETAILED DESCRIPTION OF THE INVENTION

Figure 1:
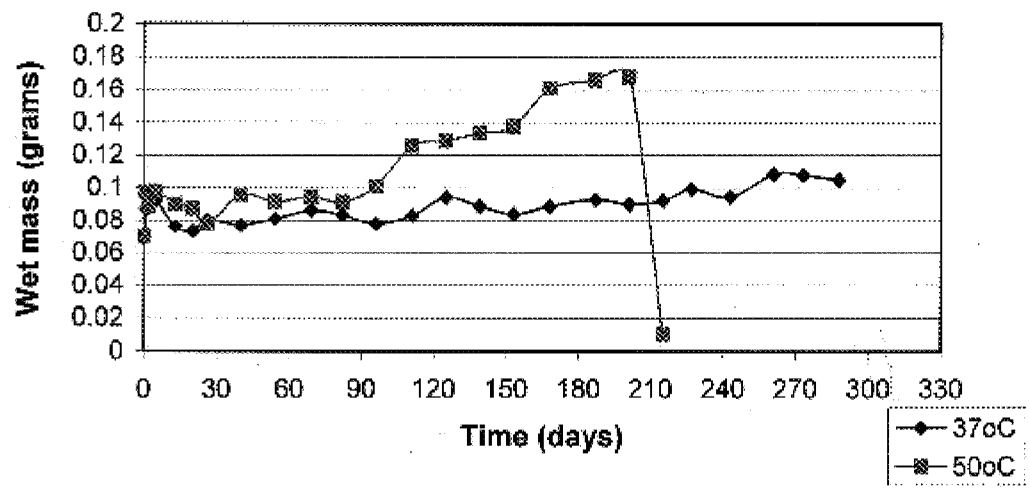
FIG. 1 illustrates the mass loss over time in pH 7.4 buffer for a hydrogel made from a 3-ester acrylate modified PVA at 1 meq/g crosslinker density. ♦ indicates the degradation at 37C; ■ indicates the degradation at 50C.

Biodegradable hydrogels based on poly(vinyl alcohol) have been developed which can be rapidly formed in an aqueous surrounding, e.g., in vivo. The PVA based hydrogels can be designed to degrade as fast as a few hours to more than 1 year. Degradation rates are determined in one respect by selection of an appropriate degradable region. For example, use of hydroxyethyl methacrylate (HEMA)-lactate as the biodegradable/crosslinkable groups will likely provide faster degradation than the use of a 3-ester methacrylate such as mono-2-(methacryoyloxy)ethyl succinate. Other factors that will affect the degradation rate are the density of the pendant chain bearing the degradable region, the length of the degradable region, the hydrophobicity of the network, and the crosslinking density.

Two Component Embodiment

In one embodiment, the hydrogels are formed by crosslinking two components. Component A is a prepolymer having a PVA backbone having pendant chains with crosslinkable groups, and component B is a molecule having a degradable region flanked by crosslinkable groups.

Component A: Prepolymer Backbone With Polymerizable Groups

PVA

The prepolymers have a backbone of a polyhydroxy polymer, such as PVA or copolymers of vinyl alcohol that contain, for example, a 1,3-diol skeleton. The backbone can also contain hydroxyl groups in the form of 1,2-glycols, such as copolymer units of 1,2-dihydroxyethylene. These can be obtained, for example, by alkaline hydrolysis of vinyl acetate-vinylene carbonate copolymers. Other polymeric diols can be used, such as saccharides.

In addition, the prepolymers can also contain small proportions, for example of up to 20%, preferably of up to 5%, of comonomer units of ethylene, propylene, acrylamide, methacrylamide, dimethacrylamide, hydroxyethyl methacrylate, alkyl (meth)acrylates, alkyl (meth)acrylates which are substituted by hydrophilic groups, such as hydroxyl, carboxyl or amino groups, methyl acrylate, ethyl acrylate, vinylpyrrolidone, hydroxyethyl acrylate, allyl alcohol, styrene, polyalkylene glycols, or similar comonomers usually used.

Polyvinyl alcohols which can be used as prepolymer backbones are commercially available PVAs, for example Vinol® 107 from Air Products (MW=22,000 to 31,000, 98–98.8% hydrolyzed), Polysciences 4397 (MW=25,000, 98.5% hydrolyzed), BF 14 from Chan Chun, Elvanol® 90-50 from DuPont and UF-120 from Unitika. Other producers are, for example, Nippon Gohsei (Gohsenol®), Monsanto (Gelvatol®), Wacker (Polyviol®) or the Japanese producers Kuraray, Deriki, and Shin-Etsu. In some cases it is advantageous to use Mowiol® products from Hoechst, in particular those of the 3-83, 4-88, 4-98, 6-88, 6-98, 8-88, 8-98, 10-98, 20-98, 26-88, and 40-88 types.

It is also possible to use copolymers of hydrolyzed or partially hydrolyzed vinyl acetate, which are obtainable, for example, as hydrolyzed ethylene-vinyl acetate (EVA), or vinyl chloride-vinyl acetate, N-vinylpyrrolidone-vinyl acetate, and maleic anhydride-vinyl acetate. If the prepolymer backbones are, for example, copolymers of vinyl acetate and vinylpyrrolidone, it is again possible to use commercially available copolymers, for example the commercial products available under the name Luviskol® from BASF. Particular examples are Luviskol VA 37 HM, Luviskol VA 37 E and Luviskol VA 28. If the prepolymer backbones are polyvinyl acetates, Mowilith 30 from Hoechst is particularly suitable.

Polyvinyl alcohols that can be derivatized in accordance with the invention preferably have a molecular weight of at least 10,000. As an upper limit, the polyvinyl alcohols may have a molecular weight of up to 1,000,000. Preferably, the polyvinyl alcohols have a molecular weight of up to 300,000, especially up to approximately 100,000 and especially preferably up to approximately 30,000.

The polyvinyl alcohols usually have a poly(2-hydroxy) ethylene structure. The polyvinyl alcohols derivatized in accordance with the disclosure may, however, also comprise hydroxy groups in the form of 1,2-glycols.

The PVA system can be a fully hydrolyzed PVA, with all repeating groups being —$CH_2$—$CH(OH)$, or a partially hydrolyzed PVA with varying proportions (25% to 1%) of pendant ester groups. PVA with pendant ester groups have repeating groups of the structure $CH_2$—$CH(OR)$ where R is $COCH_3$ group or longer alkyls, as long as the water solubility of the PVA is preserved. The ester groups can also be substituted by acetaldehyde or butyraldehyde acetals that impart a certain degree of hydrophobicity and strength to the PVA. For an application that requires an oxidatively stable PVA, the commercially available PVA can be broken down by $NaIO_4$—$KMnO_4$ oxidation to yield a small molecular weight (3–4K) PVA.

The PVAs are prepared by basic or acidic, partial or virtually complete hydrolysis of polyvinyl acetate. In a preferred embodiment, the polyvinyl alcohol derivatized in accordance with the invention comprises less than 50% of vinyl acetate units, especially less than about 25% of vinyl acetate units. Preferred amounts of residual acetate units in the polyvinyl alcohol derivatized in accordance with the invention, based on the sum of vinyl alcohol units and acetate units, are approximately from 3 to 25%.

The prepolymers contain pendant groups that can be crosslinked to one end of the component B molecules. Various crosslinkable groups can be used.

Crosslinkable Groups

Crosslinking of components may be via any of a number of means, such as physical crosslinking or chemical crosslinking. Physical crosslinking includes, but is not limited to, complexation, hydrogen bonding, desolvation, Van der wals interactions, and ionic bonding. Chemical crosslinking can be accomplished by a number of means including, but not limited to, chain reaction (addition) polymerization, step reaction (condensation) polymerization and other methods of increasing the molecular weight of polymers/oligomers to very high molecular weights. Chain reaction polymerization includes but is not exclusive to free radical polymerization (thermal, photo, redox, atom transfer polymerization, etc.), cationic polymerization (including onium), anionic polymerization (including group transfer polymerization), certain types of coordination polymerization, certain types of ring opening and metathesis polymerizations, etc. Step reaction polymerizations include all polymerizations which follow step growth kinetics including but not limited to reactions of nucleophiles with electrophiles, certain types of coordination polymerization, certain types of ring opening and metathesis polymerizations, etc. Other methods of increasing molecular weight of polymers/oligomers include but are not limited to polyelectrolyte, formation, grafting, ionic crosslinking, etc.

In one embodiment, a two part redox system is employed. One part of the system contains a reducing agent such as ferrous salt. Various ferrous salts can be used, such as ferrous gluconate dihydrate, ferrous lactate dihydrate, or ferrous acetate. The other half of the solution contains an oxidizing agent such as hydrogen peroxide. Either or both of the redox solutions can contain macromer, or it may be in a third solution. The two solutions are combined and the agents react to initiate the crosslinking.

Other reducing agents can be used, such as, but not limited to cuprous salts, cerous salts, cobaltous salts, permanganate, and manganous salts. Other oxidizing agents that can be used include, but are not limited to, t-butyl hydroperoxide, t-butyl peroxide, benzoyl peroxide, cumyl peroxide, etc.

The crosslinkable groups consist preferably of the following groups: (meth)acrylamide, (meth)acrylate, styryl, vinyl ester, vinyl ketone, vinyl ethers, etc.

Specific Prepolymers

Prepolymers suitable for use are disclosed in U.S. Pat. Nos. 5,932,674, 5,508,317, 5,665,840, 5,849,841, 6,011,077, 5,939,489, and 5,807,927.

In one embodiment, units containing a crosslinkable group conform, in particular, to the formula I

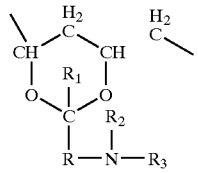

in which R is a linear or branched $C_1$–$C_8$ alkylene or a linear or branched $C_1$–$C_{12}$ alkane. Suitable alkylene examples include octylene, hexylene, pentylene, butylene, propylene, ethylene, methylene, 2-propylene, 2-butylene and 3-pentylene. Preferably lower alkylene R has up to 6 and especially preferably up to 4 carbon atoms. The groups ethylene and butylene are especially preferred. Alkanes include, in particular, methane, ethane, n- or isopropane, n-, sec- or tert-butane, n- or isopentane, hexane, heptane, or octane. Preferred groups contain one to four carbon atoms, in particular one carbon atom.

$R_1$ is hydrogen, a $C_1$–$C_6$ alkyl, or a cycloalkyl, for example, methyl, ethyl, propyl or butyl and $R_2$ is hydrogen or a $C_1$–$C_6$ alkyl, for example, methyl, ethyl, propyl or butyl. $R_1$ and $R_2$ are preferably each hydrogen.

$R_3$ is an olefinically unsaturated electron attracting copolymerizable radical having up to 25 carbon atoms. In one embodiment, $R_3$ has the structure

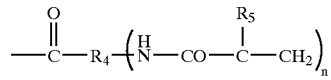

where $R_4$ is the

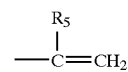

group if n=zero, or the

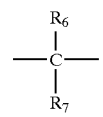

bridge if n=1;

$R_5$ is hydrogen or $C_1$–$C_4$ alkyl, for example, n-butyl, n- or isopropyl, ethyl, or methyl;

n is zero or 1, preferably zero; and $R_6$ and $R_7$, independently of one another, are hydrogen, a linear or branched $C_1$–$C_8$ alkyl, aryl or cyclohexyl, for example one of the following: octyl, hexyl, pentyl, butyl, propyl, ethyl, methyl, 2-propyl, 2-butyl or 3-pentyl. $R_6$ is preferably hydrogen or the $CH_3$ group, and $R_7$ is preferably a $C_1$–$C_4$ alkyl group. $R_6$ and $R_7$ as aryl are preferably phenyl.

In another embodiment, $R_3$ is an olefinically unsaturated acyl group of formula $R_8$—CO—, in which $R_8$ is an olefinically unsaturated copolymerizable group having from 2 to 24 carbon atoms, preferably from 2 to 8 carbon atoms, especially preferably from 2 to 4 carbon atoms. The olefinically unsaturated copolymerizable radical $R_8$ having from 2 to 24 carbon atoms is preferably alkenyl having from 2 to 24 carbon atoms, especially alkenyl having from 2 to 8 carbon atoms and especially preferably alkenyl having from 2 to 4 carbon atoms, for example ethenyl, 2-propenyl, 3-propenyl, 2-butenyl, hexenyl, octenyl or dodecenyl. The groups ethenyl and 2-propenyl are preferred, so that the group —CO—$R_8$ is the acyl radical of acrylic or methacrylic acid.

In another embodiment, the group $R_3$ is a radical of formula

[CO—NH—($R_9$—NH—CO—O)$_q$—$R_{10}$—O]$_p$—CO—$R_8$.

wherein q and q are zero or one and $R_9$ and $R_{10}$ are each independently lower alkylene having from 2 to 8 carbon atoms, arylene having from 6 to 12 carbon atoms, a saturated divalent cycloaliphatic group having from 6 to 10 carbon atoms, arylenealkylene or alkylenearylene having from 7 to 14 carbon atoms or arylenealkylenearylene having from 13 to 16 carbon atoms, and $R_8$ is as defined above.

Lower alkylene $R_9$ or $R_{10}$ preferably has from 2 to 6 carbon atoms and is especially straight-chained. Suitable examples include propylene, butylene, hexylene, dimethylethylene and, especially preferably, ethylene.

Arylene $R_9$ or $R_{10}$ is preferably phenylene that is unsubstituted or is substituted by lower alkyl or lower alkoxy, especially 1,3-phenylene or 1,4-phenylene or methyl-1,4-phenylene.

A saturated divalent cycloaliphatic group $R_9$ or $R_{10}$ is preferably cyclohexylene or cyclohexylene-lower alkylene, for example cyclohexylenemethylene, that is unsubstituted or is substituted by one or more methyl groups, such as, for example, trimethylcyclohexylenemethylene, for example the divalent isophorone radical.

The arylene unit of alkylenearylene or arylenealkylene $R_9$ or $R_{10}$ is preferably phenylene, unsubstituted or substituted by lower alkyl or lower alkoxy, and the alkylene unit thereof is preferably lower alkylene, such as methylene or ethylene, especially methylene. Such radicals $R_9$ or $R_{10}$ are therefore preferably phenylenemethylene or methylenephenylene.

Arylenealkylenearylene $R_9$ or $R_{10}$ is preferably phenylene-lower alkylene-phenylene having up to 4 carbon atoms in the alkylene unit, for example phenyleneethylenephenylene.

The radicals $R_9$ and $R_{10}$ are each independently preferably lower alkylene having from 2 to 6 carbon atoms, phenylene, unsubstituted or substituted by lower alkyl, cyclohexylene or cyclohexylene-lower alkylene, unsubstituted or substituted by lower alkyl, phenylene-lower alkylene, lower alkylene-phenylene or phenylene-lower alkylene-phenylene.

The divalent group —$R_9$—NH—CO—O— is present when q is one and absent when q is zero. Prepolymers in which q is zero are preferred.

The divalent group CO—NH—($R_9$—NH—COO)$_q R_{10}$—O— is present when p is one and absent when p is zero. Prepolymers in which p is zero are preferred.

In prepolymers in which p is one, q is preferably zero. Prepolymers in which p is one, q is zero, and $R_{10}$ is lower alkylene are especially preferred.

All of the above groups can be monosubstituted or polysubstituted, examples of suitable substituents being the following: $C_1$–$C_4$ alkyl, such as methyl, ethyl or propyl, —COOH, —OH, —SH, $C_1$–$C_4$ alkoxy (such as methoxy, ethoxy, propoxy, butoxy, or isobutoxy), —$NO_2$, —$NH_2$, —NH($C_1$–$C_4$), —NH—CO—$NH_2$, —N($C_1$–$C_4$ alkyl)$_2$, phenyl (unsubstituted or substituted by, for example, —OH or halogen, such as Cl, Br or especially I), —S($C_1$–$C_4$ alkyl), a 5- or 6-membered heterocyclic ring, such as, in particular, indole or imidazole, —NH—C(NH)—$NH_2$, phenoxyphenyl (unsubstituted or substituted by, for example, —OH or halogen, such as Cl, Br or especially I), an olefinic group, such as ethylene or vinyl, and CO—NH—C(NH)—$NH_2$.

Preferred substituents are lower alkyl, which here, as elsewhere in this description, is preferably $C_1$–$C_4$ allyl, $C_1$–$C_4$ alkoxy, COOH, SH, —$NH_2$, —NH($C_1$–$C_4$ alkyl), —N($C_1$–$C_4$ alkyl)$_2$ or halogen. Particular preference is given to $C_1$–$C_4$ alkyl, $C_1$–$C_4$ alkoxy, COOH and SH.

For the purposes of this invention, cycloalkyl is, in particular, cycloalkyl, and aryl is, in particular, phenyl, unsubstituted or substituted as described above.

Modifiers The prepolymers can include further modifier groups and crosslinkable groups such as those described in U.S. Pat. No. 5,932,674. Crosslinkable groups and the optional further modifier groups can be bonded to the prepolymer skeleton in various ways, for example through a certain percentage of the 1,3-diol units being modified to give a 1,3-dioxane, which contains a crosslinkable radical, or a further modifier, in the 2-position. Modifiers that might be attached to the hydroxyls include those to modify the hydrophobicity, active agents or groups to allow attachment of active agents, photoinitiators, modifiers such as polymers or molecules to enhance or reduce adhesiveness, polymers to impart thermoresponsiveness, polymers to impart other types of responsiveness, and additional crosslinking groups.

Component B

Component B is a molecule having a degradable region flanked by crosslinkable groups. Component B contains at least 1 group capable of crosslinking with the crosslinkable groups of component A. Component B also includes at least one group capable of crosslinking with other components B after they have been attached to component A. The mechanism by which component A crosslinks with component B can be different than the mechanism by which component B crosslinks with other component B's after they are attached to component A's. When component A is a specific prepolymer as described above, component B includes a group capable of crosslinking with the olefinically unsaturated group of component A. Component B can include other copolymers in addition to the degradable region and crosslinkable group.

Crosslinkable Groups

Any of the crosslinkable groups described above with respect to component A can also be used on component B. Different types of crosslinking may be employed for crosslinking of A to one end of B and of B with other B's.

Degradable Regions The degradable region is preferably degradable under in vivo conditions by hydrolysis. The degradable region can be enzymatically degradable. For example, the degradable region may be polymers and oligomers of glycolide, lactide, ε-caprolactone, other hydroxy acids, and other biologically degradable polymers that yield materials that are non-toxic or present as normal metabolites in the body. Preferred poly(α-hydroxy acid)s are poly (glycolic acid), poly(DL-lactic acid) and poly(L-lactic acid). Other useful materials include poly(amino acids), poly (anhydrides), poly(orthoesters), poly(phosphazines), and poly(phosphoesters). Polylactones such as poly(ε-caprolactone), poly(ε-caprolactone), poly(δ-valerolactone) and poly(γ-butyrolactone), for example, are also useful. Enzymatically degradable linkages include poly(amino acids), gelatin, chitosan, and carbohydrates. The biodegradable regions may have a degree of polymerization ranging from one up to values that would yield a product that was not substantially water soluble. Thus, monomeric, dimeric, trimeric, oligomeric, and polymeric regions may be used. The biodegradable region could, for example, be a single methacrylate group.

Biodegradable regions can be constructed from polymers or monomers using linkages susceptible to biodegradation, such as ester, acetal, carbonate, peptide, anhydride, orthoester, phosphazine, and phosphoester bonds.

Methods of Making Biodegradable PVA Hydrogels From Components A and B

Methods for Making the Prepolymers

Methods for making the prepolymers are taught in the U.S. Patents to Muller cited above.

The prepolymers of formulae I are extraordinarily stable. Spontaneous crosslinking by homopolymerization does not typically occur. The prepolymers of formula I can furthermore be purified in a manner known per se, for example by precipitation with acetone, dialysis, or ultrafiltration. Ultrafiltration is especially preferred. By means of that purification process the prepolymers of formula I can be obtained in extremely pure form, for example in the form of concentrated aqueous solutions that are free, or at least substantially free, from reaction products, such as salts, and from starting materials.

The preferred purification process for the prepolymers of the invention, ultrafiltration, can be carried out in a manner known per se. It is possible for the ultrafiltration to be carried out repeatedly, for example from two to ten times.

Alternatively, the ultrafiltration can be carried out continuously until the selected degree of purity is attained. The selected degree of purity can in principle be as high as desired. A suitable measure for the degree of purity is, for example, the sodium chloride content of the solution, which can be determined simply in known manner.

The prepolymers of formulae I are crosslinkable in an extremely effective and controlled manner.

Methods for Making Hydrogels

The methods of making a hydrogel from components A and B involves combining the components under conditions suitable for crosslinking of components A and B and, optionally in a second step, crosslinking of components B after they have been attached to components A.

The crosslinking is suitably carried out in a solvent. A suitable solvent is in principle any solvent that dissolves components A and B, for example water, alcohols, such as lower alkanols, for example ethanol or methanol, also carboxylic acid amides, such as dimethylformamide, or dimethyl sulfoxide, and also a mixture of suitable solvents, such as, for example, a mixture of water with an alcohol, such as, for example, a water/ethanol or a water/methanol-mixture. The combination of A and B is preferably carried out in a csubstantially aqueous solution. In accordance with the invention, the criterion that the prepolymer is soluble in water denotes in particular that the prepolymer is soluble in a concentration of approximately from 3 to 90% by weight, preferably approximately from 5 to 60% by weight, in a substantially aqueous solution. Insofar as it is possible in an individual case, prepolymer concentrations of more than 90% are also included in accordance with the invention.

Within the scope of this invention, substantially aqueous solutions of the prepolymer comprise especially solutions of the prepolymer in water, in aqueous salt solutions, especially in aqueous same solutions that have an osmolarity of approximately from 200 to 450 milliosmol per 1000 ml (unit: mOsm/l), preferably an osmolarity of approximately from 250 to 350 mOsm/l, especially approximately 300 mOsm/l, or in mixtures of water or aqueous salt solutions with physiologically tolerable polar organic solvents, such as, for example, glycerol. Solutions of the prepolymer in water or in aqueous salt solutions are preferred.

The viscosity of the solution of the prepolymer in the substantially aqueous solution is, within wide limits, not critical, but the solution should preferably be a flowable solution that can be deformed strain-free.

The molecular weight of the prepolymer is also, within wide limits, not critical. Preferably, however, the prepolymer has a molecular weight of from approximately 3,000 to approximately 200,000, most preferably from about 3,000 to 30,000.

Components A and B are preferably combined such that a hydrogel is formed having crosslinking in an amount of from approximately 0.25 to 10 milliequivalents of crosslinker per gram of PVA (meq/g), more desirably about 0.25 to 1,5 meq/g.

In order to encourage inter crosslinking between A and B prior to intra crosslinking of A with A or B with B, a large excess of B can be used, such as a ten fold increase. It is possible that a partially degradable hydrogel will result from this system. Such a partially degradable hydrogel may be desirable for some applications.

Preferably, the prepolymers used in the process according to the invention can be purified in a manner known per se, for example by precipitation with organic solvents, such as acetone, filtration and washing, extraction in a suitable solvent, dialysis or ultrafiltration, ultrafiltration being especially preferred. By means of that purification process the prepolymers can be obtained in extremely pure form, for example in the form of concentrated aqueous solutions that are free, or at least substantially free, from reaction products, such as salts, and from starting materials, such as, for example, non-polymeric constituents.

The preferred purification process for the prepolymers used in the process according to the invention, ultrafiltration, can be carried out in a manner known per se. It is possible for the ultrafiltration to be carried out repeatedly, for example from two to ten times. Alternatively, the ultrafiltration can be carried out continuously until the selected degree of purity is attained. The selected degree of purity can in principle be as high as desired. A suitable measure for the degree of purity is, for example, the sodium chloride content of the solution, which can be determined simply in a known manner, such as by conductivity measurements.

One additive that is added, where appropriate, to the solution of the prepolymer is an initiator for the crosslinking, should an initiator be required for crosslinking the crosslinkable groups. Moreover, it may be desirable to employ different crosslinking means for crosslinking component A to component B and for crosslinking component B to other component B's after they are attached to component A's. For example, it may be desirable to employ salt crosslinking for crosslinking component A to component B but to employ redox initiated free radical crosslinking for crosslinking components B.

Single Component Embodiment

In the single component embodiment, a prepolymer is used to produce the hydrogel. The prepolymer includes a PVA backbone having pendant chains having a degradable region and crosslinkable group. In this embodiment, as opposed to the two component embodiment, the biodegradable regions are attached to the PVA backbone to form a prepolymer prior to crosslinking of the prepolymer into a hydrogel. It is desired that at least a majority of the crosslinkable groups are attached to the polymer via the degradable region. The prepolymer when polymerized results in a crosslinked network that is permeable to water but water insoluble. This crosslinked PVA network has degradable segments in between the crosslinked moieties. As such, hydrolytic/enzymatic degradation of these degradable segments would result in the degradation of the entire network, or a degradable PVA system.

The degradable segment may be attached to the backbone in two ways. One method involves the preparation of a degradable crosslinker containing both the polymerizable segment and the degradable segment, followed by its attachment to the PVA backbone. The attachment of the degradable crosslinker to the backbone can be done by suitable functionalization of pendant hydroxyl groups on the PVA backbone and/or the degradable crosslinker.

A second method involves the attachment of the degradable segment first to the PVA backbone, following which the crosslinkable moiety is attached to the degradable segment. The ease of synthesis as well as the type of degradable segment and crosslinker used determines the type of method used. The choice of a suitable degradable segment, its length and loading dictate the final degradation profile achieved, although this is also a function of certain environmental factors such as pH, temperature and buffer concentrations.

The PVA Backbone

Generally, the requirements for the PVA in this embodiment are the same as for the two component embodiment. Poly(vinyl alcohols) which can be used as prepolymer backbones are commercially available PVAs, for example Vinol® 107 from Air Products (MW=22,000 to 31,000, 98–98.8% hydrolyzed), Polysciences 4397 (MW=25,000, 98.5% hydrolyzed), BF 14 from Chan Chun, Elvanol® 90-50 from DuPont and UF-120 from Unitika. Other producers are, for example, Nippon Gohsei (Gohsenol®), Monsanto (Gelvatol®), Wacker (Polyviol®) or the Japanese producers Kuraray, Deriki, and Shin-Etsu. In some cases it is advantageous to use Mowiol® products from Hoechst, in particular those of the 3-83, 4-88, 4-98, 6-88, 6-98, 8-88, 8-98, 10-98, 20-98, 26-88, and 40-88 types.

It is also possible to use copolymers of hydrolyzed or partially hydrolyzed vinyl acetate, which are obtainable, for example, as hydrolyzed ethylene-vinyl acetate (EVA), or vinyl chloride-vinyl acetate, N-vinylpyrrolidone-vinyl acetate, and maleic anhydride-vinyl acetate. If the prepolymer backbones are, for example, copolymers of vinyl acetate and vinylpyrrolidone, it is again possible to use commercially available copolymers, for example the commercial products available under the name Luviskol® from BASF. Particular examples are Luviskol VA 37 HM, Luviskol VA 37 E and Luviskol VA 28. If the prepolymer backbones are polyvinyl acetates, Mowilith 30 from Hoechst is particularly suitable.

The PVA should preferably have a molecular weight of at least 10,000. As an upper limit, the polyvinyl alcohols may have a molecular weight of up to 1,000,000. Preferably, the polyvinyl alcohols have a molecular weight of up to 300,000, especially up to approximately 100,000 and especially preferably up to approximately 30,000.

PVAs usually have a poly(2-hydroxy)ethylene structure. The PVA may, however, also comprise hydroxy groups in the form of 1,2-glycols.

The PVA system can be a fully hydrolyzed PVA, with all repeating groups being —$CH_2$—CH(OH), or a partially hydrolyzed PVA with varying proportions (25% to 1%) of pendant ester groups. PVA with pendant ester groups have repeating groups of the structure $CH_2$—CH(OR) where R is $COCH_3$ group or longer alkyls, as long as the water solubility of the PVA is preserved. The ester groups can also be substituted by acetaldehyde or butyraldehyde acetals that impart a certain degree of hydrophobicity and strength to the PVA. For an application that requires an oxidatively stable PVA, the commercially available PVA can be broken down by $NaIO_4$—$KMnO_4$ oxidation to yield a small molecular weight (3–4K) PVA.

The PVA is prepared by basic or acidic, partial or virtually complete hydrolysis of polyvinyl acetate. In a preferred embodiment, the polyvinyl alcohol derivatized in accordance with the invention comprises less than 50% of vinyl acetate units, especially less than 20% of vinyl acetate units. Preferred amounts of residual acetate units in the polyvinyl alcohol derivatized in accordance with the invention, based on the sum of vinyl alcohol units and acetate units, are approximately from 3 to 20%, preferably approximately from 5 to 16%.

Depradable Region

Generally the same degradable regions can be used as are described above for the two component embodiment. The PVA based hydrogels can be designed to degrade as fast as an hour to a day (with cross linkers containing rapidly degradable segments such as HEMA-glycolate and HEA-glycolate), to a few days or more than 1 year, with degradable segments such as 3-ester or 5-ester methacrylates or acrylates (for example, using mono-2-(methacryloyloxy) ethyl succinate (a 3-ester methacrylate), or mono-2-(Acryloyloxy)ethyl succinate (AOES, a 3-ester acrylate).

The desired degradability can be achieved using an appropriate degradable region, an appropriate region length, by varying the hydrophobicity of the network with pendant groups, and by varying the density or loading of the degradable/crosslinking chains.

Crosslinkable Groups

The crosslinkable groups that can be used in the single component embodiment are the same as those described above with respect to the two component embodiment.

Modifiers

The prepolymers can include further modifier groups and crosslinkable groups such as those described in U.S. Pat. No. 5,932,674. Crosslinkable groups and the optional further modifier groups can be bonded to the prepolymer skeleton in various ways, for example through a certain percentage of the 1,3-diol units being modified to give a 1,3-dioxane, which contains a crosslinkable radical, or a further modifier, in the 2-position. Modifiers that might be attached to the hydroxyls include those to modify the hydrophobicity, active agents or groups to allow attachment of active agents, photoinitiators, modifiers such as polymers or molecules to enhance or reduce adhesiveness, polymers to impart thermoresponsiveness, polymers to impart other types of responsiveness, and additional crosslinking groups.

Methods of Making Biodegradable PVA Hydrogels From a Single Component

The prepolymers can be made in at least two ways. In one method, a degradable crosslinker containing both the polymerizable group and the degradable region is prepared, followed by its attachment to the PVA backbone. The attachment of the degradable cross linker to the backbone can be done by suitable functionalization of pendant hydroxyl groups on the PVA backbone and/or groups on the degradable cross linker. In a second method, the degradable segment is first attached to the PVA backbone, following which the cross linkable moiety is attached to the degradable segment.

The methods for attaching the crosslinkable group to the degradable region and for attaching the degradable region to the PVA will vary according to the type of crosslinkable group and degradable region used. One skilled in the art will be capable of designing a synthetic scheme.

Degradable glycolide or lactide based crosslinkers can be prepared according to the reference Furch, M. et al., Polymer, 39(10):1977–1982 (1998). It should be noted that this experimental procedure offers several advantages. First, a variety of degradable segments derived from glycolide, lactide, caprolactone, cyclic anhydrides, etc. can be prepared each of which provides a specific degradation profile. Second, this technique also allows for a "1-step" synthesis of a degradable cross linker by simple control of the initial "feed ratio" of monomer to initiator. Third, by supplying a feed of different monomer types and monomer ratios, one could prepare a variety of random or block copolymers to achieve a specific degradation pattern. Fourth, one could incorporate end cappers such as succinic anhydride in the initial monomer feed to prepare acid-terminated segments, thereby eliminating an additional synthetic step.

Methods for Using the Prepolymers and Hydrogels

The hydrogels can be used for a number of biomedical applications, including, but not limited to, implants, embolic agents, wound healing dressings, adhesion prevention, sealants, bulking agents, coatings for biomaterials, and delivery of biologically active compounds such as drugs, genes, proteins, and enzymes.

In one embodiment, a hydrogel is formed from the prepolymers prior to implantation in or application or administration to a patient. In another embodiment, a hydrogel is formed in situ at the intended site of use. By way of example, a soft tissue implant can be formed by injecting a solution of prepolymers into the site where the implant is to be formed, along with the second component if the two component embodiment is used. Crosslinking of the prepolymers is initiated to form the hydrogel. Bulking agents and embolic agents can be similarly formed. The compositions can also be used to create tissue supports by forming shaped articles within the body to serve a mechanical function. Such supports include, for example, sealants for bleeding organs, sealants for bone defects and space-fillers for vascular aneurysms. Further, such supports include strictures to hold organs, vessels or tubes in a particular position for a controlled period of time.

The compositions can be applied in a number of ways, such as injection, via catheter, by spray, by pouring or spreading on a surface.

The composition can be used for encapsulation of various agents, such as therapeutic, diagnostic and prophylactic agents. For example, the compositions can be used to deliver an active agent which can be any of a variety of materials, including proteins, carbohydrates, nucleic acids, and inorganic and organic biologically active molecules. Specific examples include enzymes, antibiotics, antineoplastic agents, local anesthetics, hormones, antiangiogenic agents, antibodies, neurotransmitters, psychoactive drugs, drugs affecting reproductive organs, and oligonucleotides such as antisense oligonucleotides. Cells, tissues, and organelles can also be encapsulated.

In a variation of the method for controlled drug delivery, the prepolymers are polymerized with the biologically active materials to form microspheres or nanoparticles containing the biologically active material. The macromer, photoinitiator, and agent to be encapsulated are mixed in an aqueous mixture. Particles of the mixture are formed using standard techniques, for example, by mixing in oil to form an emulsion, forming droplets in oil using a nozzle, or forming droplets in air using a nozzle. The suspension or droplets are irradiated with a light suitable for photopolymerization of the macromer.

The present invention will be further understood by reference to the following non-limiting examples.

EXAMPLES
Moderate to Slow Degrading Systems

Hydrogels having moderate to slow degradation times, ranging from a few days, to months, to a year were prepared. Degradation profiles are shown in Tables 1 and 2.

Example 1

Preparation of Degradable PVA Containing 3-Ester Acrylate Cross Linker 3-ester acrylate modified PVA was prepared having 0.5 to 1.8 milliequivalents of the side chain per gram of PVA (meq/g). The following recipe is for 1.0 meq/g. The proportion of crosslinker chain to PVA was adjusted to prepare prepolymers with other meq/g. Dried mono-2-(acryloyloxy) ethyl succinate (AOES, 2.3 g, 10.6 mmoles) in dichloromethane (DCM, 35 mL) was maintained under nitrogen at about 5° C. One glass stopper was removed and replaced with a rubber septum. Dicyclohexylcarbodiimide (DCC) solution (5 mL, 5 mmoles) was removed from the sure seal bottle by syringe under nitrogen flow. The DCC solution was added to the AOES solution slowly over about 2 minutes. A precipitate formed almost immediately. After complete addition of the DCC solution, the flask was removed from the ice bath and the solution was stirred at room temperature. The reaction was followed by the disappearance of the DCC peak at about 2116 cm$^{-1}$. The reaction was done in less than 2 hours.

When the reaction was complete, the dicyclohexylurea (DCU) byproduct was removed by filtration through a glass frit. The precipitate was rinsed with a little DCM and the DCM was removed from the filtrate using the rotary evaporator. About 5 mL or more of DMSO was added as needed in order to dissolve the anhydride. At this time, 29.4 g of an 18% PVA solution in DMSO was added. The PVA used was Mowiol 3-83. Upon addition of the PVA solution, some polymer may precipitate. If this does occur, stir the solution until the solution is homogenous. Heating the solution to 60° C. may be required. When the solution was homogeneous, 5 drops of triethylamine was added. The solution was stirred at room temperature overnight. The following day, the solution was heated to 60° C. for 1 hour. The solution was precipitated into a 10-fold excess of acetone (vs. volume of DMSO). Additional DMSO may be needed to dilute the solution so the polymer is able to precipitate adequately. About 12–15% solids is appropriate.

Formulation, Casting, and Curing of Degradable PVA

A 20% solution of the degradable PVA prepolymers in water was prepared with 0.3% Irgacure. The mixture was warmed to 60° C. for about 15–30 minutes until the polymer completely dissolved. To prepare flats, 2 drops of the polymer solution were transferred into a polypropylene mold, the mold was closed, and the solution was irradiated for 20 seconds (2.0–2.5 mW/cm$^2$ at 310 nm, and intensity of 65–75 mW/cm$^2$ at 365 nm). Plugs were prepared by adding 35 drops of the formulation to the open male end of the polypropylene mold and irradiating under the same conditions. The cross linked gels were analyzed for degradation profiles.

Protocol for In vitro Degradation Experiments

A 10 mM HEPES solution at pH 7.4 was prepared containing 0.200 g/L sodium azide. The phosphate buffer used was a 100 mM solution at pH 9.0 containing 0.200 g/L sodium azide.

Determination of Initial Wet Weight

Prior to the degradation experiment, the gels were stored in USP water at 4° C. A gel sample was removed from solution using small forceps. The excess water was removed from the gel by touching the sample to the side of the beaker. The sample was then placed in a vial, the lid placed on the vial and weighed on a 4-place balance.

Determination of the Initial Dry Weight

After the wet weight of the samples has been determined the lid was removed and the samples were exposed in order for it to start to dry. A few pieces of dry ice were placed in a small Dewar flask. Ethanol was slowly added to the dry ice. Wait until the evolution of $CO_2$ has slowed before beginning. The vial was held without the lid using crucible tongs and about 1 cm of the bottom of the vial was submerged into the cold ethanol for 1 minute. At this time the vial was removed from the cold ethanol, the excess ethanol was dried from the bottom of the vial using a paper towel and the vial was placed in the freezer and kept there for at least 1 hour. The samples were placed into the freeze-drier overnight. The next day, the dried samples were weighed with the lids on.

General Procedure

After the weights were determined, 5 mL of the appropriate buffer was immediately added using a 10 mL pipet. The lid was replaced and the vial was placed into the appropriate oven.

When a mass measurement was taken, the vial was removed from the oven and allowed to cool for a few minutes, then a small plastic pipet was used to remove the excess water without touching the sample. After all the excess water was removed, all the excess water from the lid and inside the vial was removed without touching the sample. The lid was replaced and the weight of the sample was determined as described above for the wet weight determination. After this was done, either some fresh HEPES solution was added to the vial or the sample was freeze-dried and the dry weight of the sample was determined.

FIG. 1 illustrates the mass loss over time in pH 7.4 buffer for a hydrogel made from a 3-ester acrylate modified PVA at 1 meq/g crosslinker density. ♦ indicates the degradation at 37C; ■ indicates the degradation at 50C.

Figure 2:
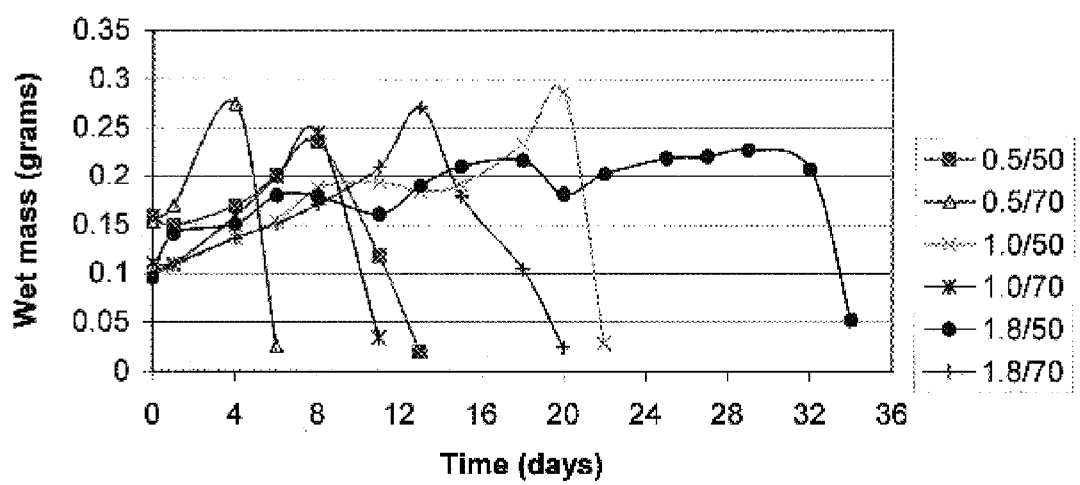
FIG. 2 illustrates the mass loss for a hydrogel made from 3-ester acrylate modified PVA in pH 9.0 buffer. ■ indicates the degradation at 0.5 meq/g crosslinker density and 50C; Δ indicates the degradation at 0.5 meq/g crosslinker density and 70C; x indicates the degradation at 1.0 meq/g crosslinker density and 50C; * indicates the degradation at 1.0 meq/g crosslinker density and 70C; ● indicates the degradation at 1.8 meq/g crosslinker density and 50C; and | indicates the degradation at 1.8 meq/g crosslinker density and 70C.

FIG. 2 illustrates the mass loss for a hydrogel made from 3-ester acrylate modified PVA in pH 9.0 buffer. ■ indicates the degradation at 0.5 meq/g crosslinker density and 50C; Δ indicates the degradation at 0.5 meq/g crosslinker density and 70C; x indicates the degradation at 1.0 meq/g crosslinker density and 50C; * indicates the degradation at 1.0 meq/g crosslinker density and 70C; ● indicates the degradation at 1.8 meq/g crosslinker density and 50C; and | indicates the degradation at 1.8 meq/g crosslinker density and 70C.

Example 2

Preparation of Degradable PVA Containing 3-Ester Methacrylate Cross Linker

The same procedure as Example 1 was followed, using mono-2-(methacryloyloxy)ethyl succinate.

Figure 3:
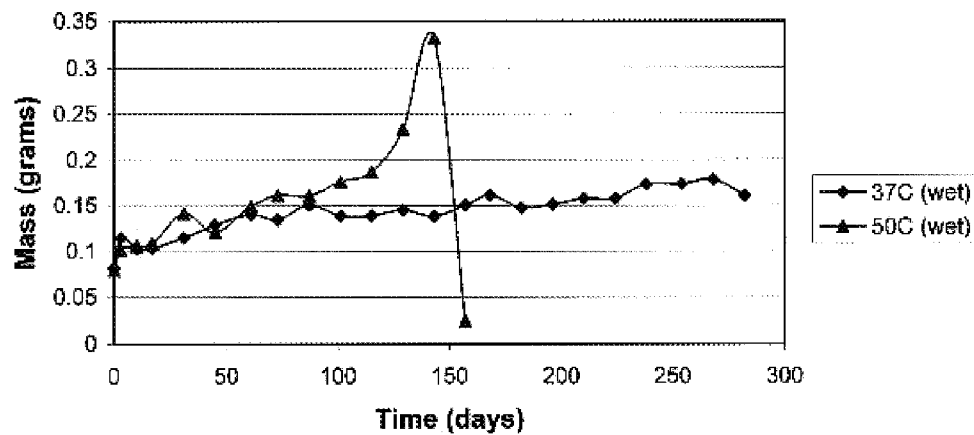
FIG. 3 illustrates the mass loss for a hydrogel made from 3-ester methacrylate modified PVA at 1 meq/g crosslinker density in pH 7.4 buffer. ♦ indicates an average wet weight of four samples at 37C (wet); ▼ indicates the degradation at 50C (wet); ■ indicates the degradation at 37C (dry); and x indicates the degradation at 50C (dry).

FIG. 3 illustrates the mass loss for a hydrogel made from 3-ester methacrylate modified PVA at 1 meq/g crosslinker density in pH 7.4 buffer. ♦ indicates an average wet weight of four samples at 37C (wet); ▼ indicates the degradation at 50C (wet); ■ indicates the degradation at 37C (dry); and x indicates the degradation at 50C (dry).

Example 3

Preparation of Degradable PVA Containing 5-Ester Acrylate Cross Linker

AOES (3 g, 13.88 mmoles) and ethylene glycol (4.308 g, 69.4 mmoles) were dried. A few milligrams of dimethylaminopyridine (DMAP) was added to the solution. The solution was cooled to 4° C., and 1M DCC solution (13.88 mL, 13.88 mmoles) was added over 25 minutes. At this time the solution was removed from the ice bath and stirred at room temperature for 4 hours. The DCU precipitate was removed by filtration and the filtrate was extracted with 5% HCl (2×75 mL), 1 M NaHCO$_3$ (2×75 mL) and deionized water (2×5 mL). The organic phase was dried with MgSO$_4$, the MgSO$_4$ was filtered, and the filtrate concentrated under reduced pressure. The product was dried overnight in a vacuum oven at room temperature.

The product of the above reaction (0.915 g, 3.52 mmoles) was dissolved in 10 mL of dichloroethane (DCE). Succinic anhydride (0.352 g, 3.52 mmoles) and 1-methylimidazole (72 μL) was added to the solution. The solution was heated to 60° C. for 3 hours, then cooled to room temperature, and extracted with 10% HCl (2×50 mL) and deionized water (2×50 mL). The organic layer was dried using MgSO$_4$, the MgSO$_4$ was filtered, and the filtrate concentrated under reduced pressure. The product was dried in a vacuum oven overnight at room temperature. $^1$H NMR CDCl$_3$ (vinyl, 6.4 ppm (d), 6.2 ppm (q), 5.8 ppm (d); CH$_2$ of ethylene glycol, 4.2–4.4 ppm; CH$_2$ of succinic acid, 2.6–2.8 ppm). FT-IR (COOH, 2300–3600 cm$^{-1}$; ester, 1732 cm$^{-1}$; vinyl, 2957, 1636 cm$^{-1}$).

5-ester acrylate having 3 meq/g acetal was prepared similarly.

Figure 4:
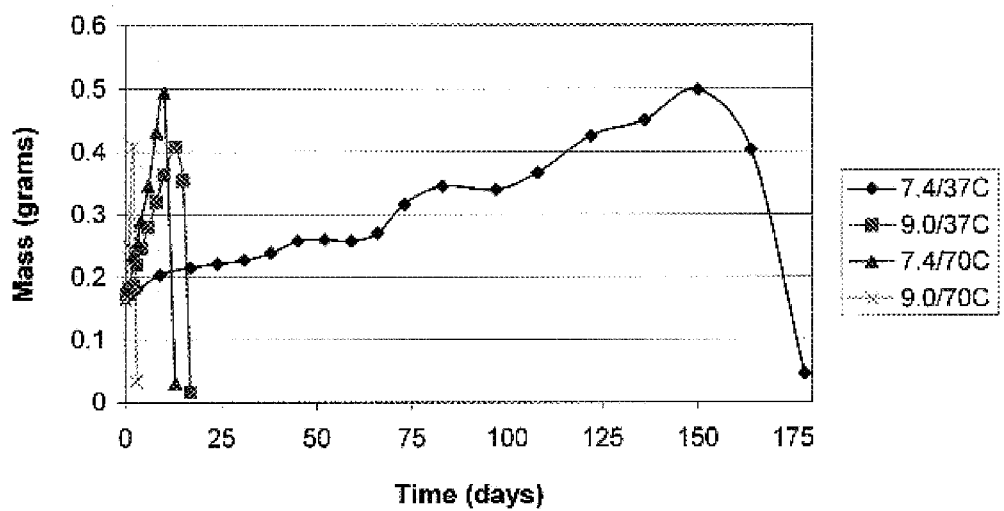
FIG. 4 illustrates the mass loss for a hydrogel made from 5-ester acrylate modified PVA at 1 meq/g crosslinker density in 10 mM HEPES buffer at pH 7.4 and pH 9.0. ♦ indicates the degradation at 37C and pH 7.4; ■ indicates the degradation at 37C and pH 9.0; ▼ indicates the degradation at 70C and pH 7.4; and x indicates the degradation at 70C and pH 9.0.

FIG. 4 illustrates the mass loss for a hydrogel made from 5-ester acrylate modified PVA at 1 meq/g crosslinker density in 10 mM HEPES buffer at pH 7.4 and pH 9.0. ♦ indicates the degradation at 37C and pH 7.4; ■ indicates the degradation at 37C and pH 9.0; ▼ indicates the degradation at 70C and pH 7.4; and x indicates the degradation at 70C and pH 9.0.

Figure 5:
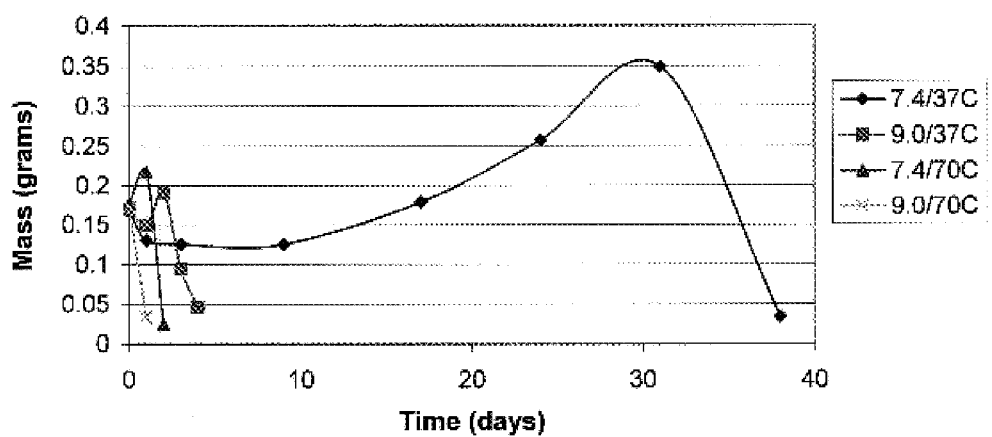
FIG. 5 illustrates the mass loss for a hydrogel made from 5-ester acrylate modified PVA at 1 meq/g crosslinker density in 0.1 M phosphate buffer at pH 7.4 and pH 9.0. ♦ indicates the degradation at 37C and pH 7.4; ■ indicates the degradation at 37C and pH 9.0; ▼ indicates the degradation at 70C and pH 7.4; and x indicates the degradation at 70C and pH 9.0.

FIG. 5 illustrates the mass loss for a hydrogel made from 5-ester acrylate modified PVA at 1 meq/g crosslinker density in 0.1 M phosphate buffer at pH 7.4 and pH 9.0. ♦ indicates the degradation at 37C and pH 7.4; ■ indicates the degradation at 37C and pH 9.0; ▼ indicates the degradation at 70C and pH 7.4; and x indicates the degradation at 70C and pH 9.0.

Example 4

Preparation of Degradable PVA Containing Carboxyethylacrylate Cross Linker

The same procedure as Example 1 was followed using carboxyethylacrylate and 3-83 PVA at 1.0 meq/g.

Example 5

Preparation of Degradable PVA Containing Vinyl Azlactone Cross Linker

The same procedure as Example 1 was followed using vinylazlactone and 4-88 PVA at 1.0 meq/g. Azlactone-modified PVA was prepared according to the literature reference Muhlebach, A. el. al., *J. Polym. Sci., Polym. Chem. Ed.* 1997, 35, 3603–3611.

Example 6

Preparation of Degradable PVA Containing 10K PEG Diazlactone Cross Linker

PEG 10K diol (10 g) was dissolved in 52 mL DCM. The material was dried by reflux of DCM through molecular sieves for an hour. Vinyl azlactone (0.5105 g, 0.0037 moles) was added to the PEG solution, followed by 20 μl of 1,8-diazabicyclo{5,4,0}undec-7-ene (DBU). The solution was heated under reflux for 24 hours. After the solution cooled, it was poured into 500 mL of hexane. The precipitate was filtered and dried in a vacuum oven at room temperature overnight.

TABLE 1

Days to Complete Degradation in 0.1M Phosphate Buffer

| Crosslinker | days at pH 7.4 37° C. | days at pH 9.0 37° C. | days at pH 7.4 70° C. | days at pH 9.0 70° C. | days in 1N NaOH | Diameter in PBS (37° C.) |
|---|---|---|---|---|---|---|
| 3-ester acrylate flat (1.0 meq/g) | 105[1] | 12–14 | 4 | 2 | — | |
| 3-ester acrylate plug (1.25 meq/g) | >76 | — | — | — | — | |
| 3-ester methacrylate (1.0 meq/g) | >178 | 33–35 | 8–8.5 | 3 | 2–3 minutes | |
| 5-ester acrylate flat (1.0 meq/g) | 36–38 | 2 | 1.7 | 0.5 | — | |
| 5-ester acrylate plug (1.5 meq/g) | >86 | — | — | — | — | 19 mm |
| 5-ester acrylate plug (1.3 meq/g) | 69 | — | — | — | — | 18 mm (hazy) |
| 5-ester acrylate plug (0.75 meq/g) | 46 | 15–17 | — | — | — | — |
| 5-ester acrylate plug (0.5 meq/g) | 25–26 | — | 1.3 | — | — | 21 mm |
| 5-ester acrylate plug (0.4 meq/g) | 13–14 | — | — | — | — | 22 mm |
| 5-ester acrylate plug (0.34 meq/g) | 8–13 | — | — | — | — | 30 mm |
| 5-ester acrylate plug (0.4 meq/g + 3 meq/g acetal) | >38 | — | — | — | — | 18 mm |
| 5-ester acrylate plug (0.3 meq/g + 3 meq/g acetal) | >35 | — | 4[2] | — | — | 20 mm |
| Carboxyethyl-acrylate | >188 | >188 | >188 | >188 | 5 | |
| Vinyl azlactone | >185 | >185 | >185 | >193 | 7 hours | |
| PEG 10K diazlactone | 57,65 | >145 | 7 | 3.5 | ~38 minutes | |
| PEG 35K diacrylate | — | 16 hours | — | 1–5 hours | 5 seconds | |

Note 1: gels not completely degraded, but unable to remove buffer solution without removing the pieces of gel.
Note 2: The sample held its shape for 4 days at 70° C., but lost its shape when cooled to room temperature

TABLE 2

Days to Complete Degradation in 10 mM HEPES Buffer

| Crosslinker | days at pH 7.4 37° C. | days at pH 9.0 37° C. | days at pH 7.4 70° C. | days at pH 9.0 70° C. | Comments |
|---|---|---|---|---|---|
| 3-ester methacrylate (1 meq/g) | >281 | — | 94–104 | — | 33% mass increase in 274 days |
| 3-ester acrylate (1 meq/g) | >273 | — | — | 11 | 73% mass increase in 272 days |
| 5-ester acrylate (1 meq/g) | 178 | 15–17 | 13 | 2.5 | Some sample pieces left |

Fast Degrading Systems

Hydrogels having fast degradation times, ranging from hours to a day were prepared. Degradable glycolide cross linkers were prepared according to the reference Furch, M. et al., Polymer, 39(10):1977–1982 (1998).

Materials:

Glycolide obtained from PolySciences was used as received. Hydroxyethyl acrylate (HEA) and Hydroxyethyl methacrylate (HEMA) were dried over molecular sieves (4 A) and distilled under reduced pressure before use. Triethyl aluminum (Et$_3$Al, 1M solution in hexane) was obtained from Aldrich and used as received. Triethyl aluminum (Et$_3$Al, 2M solution in toluene) was obtained from Aldrich and used as received. Anhydrous methylene chloride (DCM, >99.9%, Aldrich), anhydrous DMSO (Aldrich), and diethyl ether were used as received. All glassware was dried in the oven, and flame dried under nitrogen flow before use. All transfers were done under strictly anhydrous conditions via syringe or cannula.

Example 7

Preparation of Degradable PVA Containing HEMA Glycolate-COOH Cross Linker

Preparation of HEMA-Glycolate-COOH Cross Linker

HEMA-glycolate-OH (F.W. 246 g/mol, 5 g, 20 mmol) was taken in a 3-necked flask fitted with a water condenser. Succinic anhydride (3.15 g, 30.5 mmol), a pinch of 4-methoxyphenol, and 200 mL of anhydrous dichloroethane (DCE) were added to the above reaction flask and the contents were stirred. 1-methyl imidazole(3.5 mL, 44 mmol) was added to the above reaction flask and the contents were stirred overnight (~18 h) at 70° C. using an oil bath. The mixture was cooled to room temperature and transferred to a separatory funnel. The contents were washed with 10% HCl (2×100 mL), followed by DI water (2×100 mL). Saturated NaCl was used to break up any emulsions in the course of the work up. The organic layer (DCE) was separated, dried over MgSO$_4$, and the MgSO$_4$ filtered off. The filtrate was concentrated on a rotary evaporator to yield the HEMA-glycolide-COOH product as yellow oil. The product was characterized by IR, Proton NMR and Carbon NMR spectroscopy. $^1$H NMR (CDCl$_3$) 6.3 ppm (d, 1H) of vinyl, 5.6 ppm (d, 1H) of vinyl, 4.6–4.8 ppm (m, 4H) of CH$_2$ of glycolate unit, 4.4 ppm (m, broad, 4H) includes CH$_2$ groups of HEMA, 2.6–2.8 ppm (m, 4H) of succinic anhydride end-capper, 2.0 ppm (s, 3H) of CH$_3$ group of HEMA.

Preparation of Degradable PVA Containing HEMA-Glycolate-COOH Cross Linker

The HEMA-glycolate-COOH cross linker was attached to PVA by the following procedure. 60 mL of DCM was taken in a flame dried 3-necked flask fitted with a Soxhlet and a condenser (attached to the Soxhlet). The Soxhlet was pre-filled with dry molecular sieves. The contents were refluxed for 2.5 h. The HEMA-glycolate-COOH (F.W. 346 g/mol, 2.0 g, 5.8 mmol) in 20 mL of anhydrous DCM was added to the reaction flask by syringe and the contents were gently refluxed for an additional 0.5 h. The contents were cooled to room temperature and dicyclohexylcarbodiimide (1M solution in DCM, 2.9 mL, 2.9 mmol) was added in drops to the reaction flask by syringe. The mixture remained clear but turned turbid in a few minutes due to the precipitation of the dicyclohexyl urea byproduct. The contents were stirred at room temperature for 3 h, and the reaction was followed for completion by IR analysis. The contents were filtered to remove the urea byproduct and the filtrate was concentrated on a rotary evaporator. The residue obtained after concentration is the anhydride of HEMA-glycolate-COOH. This product was taken in about 100 mL of anhydrous DMSO and the contents were stirred.

Poly(vinyl alcohol) [PVA 4-88, 14.2 g, 20% solution in anhydrous DMSO] was taken in a dry flask and 80 mL of DMSO was added to the flask by cannula. Triethyl amine (2 mL) was added to the PVA solution and the contents were stirred for ~5 minutes. Following this, the anhydride product in DMSO (prepared above) was cannulated in drops to the PVA solution with rapid stirring. The contents were stirred overnight at room temperature, and then for 2 h at 60° C. using an oil bath. The contents were cooled to room temperature and the DMSO solution of PVA was precipitated into acetone (DMSO:acetone was 1:10, v/v) in drops with rapid stirring. A fine white precipitate was obtained that was isolated by filtration or centrifuging process (dependent on the type of precipitate obtained). The precipitate was then dried under vacuum to yield a dry white fibrous solid which is the degradable PVA containing the HEMA-glycolate cross linker (loading of degradable segment on PVA is 1 meq/g).

Formulation, Casting, and Curing of Degradable P VA

A 30% solution of the degradable PVA prepolymer in water was prepared with 1% Irgacure. The mixture was warmed to 60° C. for about 15–30 minutes until the polymer completely dissolved. The polymer solution was then transferred into polypropylene molds and UV irradiated for 30 seconds (2.0–2.5 mW/cm$^2$ at 310 nm, and intensity of 65–75 mW/cm$^2$ at 365 nm) to yield a cross linked gel that was analyzed for degradation profiles. The degradation profiles were determined as described below. After UV irradiation, the flats were placed in a suitable buffer at a specific temperature and the time to dissolution was determined. A static set up was used.

The degradation times of this hydrogel in various buffers at various temperatures is shown in Table 3. The phosphate buffer used was a 100 mM solution at pH 9.0 (with 0.2% NaN$_3$). The HEPES buffer used was a 10 mM solution at pH 9.0 (without 0.2% NaN3). Materials used were flats that were cured by UV light for 30 seconds, in polypropylene molds of 246 um thickness. Loading of cross linker groups (XL) on PVA was 1 meq/g.

TABLE 3

Degradation of [PVA-glycolate-XL] as a function of buffer type and temperature

| Buffer | Temperature (° C.) | Buffer Volume (mL) | Time to Degradation (hours) | Gel Form |
|---|---|---|---|---|
| Phosphate | 37 | 10 | 5.50 | Dissolved |
| Phosphate | 37 | 10 | 5.50 | Dissolved |
| Phosphate | 50 | 10 | 3.50 | Dissolved |
| Phosphate | 50 | 10 | 3.50 | Dissolved |
| Phosphate | 70 | 10 | 3.35 | Dissolved |
| Phosphate | 70 | 10 | 3.35 | Dissolved |
| HEPES | 37 | 10 | 29.0 | Dissolved |
| HEPES | 37 | 10 | 29.0 | Dissolved |
| HEPES | 50 | 10 | 20.0 | Dissolved |
| HEPES | 50 | 10 | 20.0 | Dissolved |
| HEPES | 70 | 10 | 3.33 | Dissolved |
| HEPES | 70 | 10 | 3.33 | Dissolved |

Example 8

Preparation of Degradable PVA Containing HEA-Glycolate Cross Linker

Synthesis of HEA-Glycolate-OH 60 mL of DCM and Et$_3$Al solution in toluene (2 M solution, 1.5 mL, 3 mmol) were placed in a flask that had been flame dried and purged with nitrogen, and equipped with a rubber septum. The contents in the flask were cooled to 0° C. for about 15 minutes. Under vigorous stirring, freshly distilled hydroxyethyl acrylate (HEA) (0.4 mL, 3 mmol) in 15 mL of DCM was added by cannula to the flask containing the Et$_3$Al solution. The color of the solution turned yellow on addition of the HEA and stayed yellow for a few seconds. The contents were stirred at 0° C. for 10 minutes and then at room temperature for 1 h. The flask was then transferred to an oil bath and stirred at 40° C. for an additional 30 minutes. Glycolide (3.5 g, 30 mmol) was quickly weighed out into a clean dry flask with a stir bar and the flask was sealed with a rubber septum. About 90 mL of DCM was cannulated into the flask containing the glycolide and the contents were stirred to effect dissolution. The glycolide solution was then cannulated into the flask containing the HEA-Et$_3$Al solution at 40° C. The contents of the flask remained clear during this addition but became turbid with progress of the reaction. The contents were allowed to stir for 20 h at room temperature. At the end of the reaction, trifluoroacetic acid (in this case, 120 mL) was added to the reaction mixture with vigorous stirring until most of the prepolymer dissolved (external cooling may be employed at this stage of the reaction if necessary). On addition of the trifluoroacetic acid, the turbid mixture became increasingly translucent. The mixture was then filtered through a coarse frit funnel and precipitation of the filtrate was checked in diethyl ether. The entire filtrate (about 230 mL) was added in drops to diethyl ether (800 mL) with rapid stirring to yield a white precipitate. The precipitate was filtered using a frit funnel under aspirator pressure and the product was dried in a vacuum oven overnight at room temperature. Carbon NMR and Proton NMR characterization confirms the formation of the product i.e. HEA attached to 20 glycolate units (from 10 glycolide units). $^1$H NMR (CDCl$_3$/CF$_3$COOD mixture) 6.6 ppm (d) of vinyl, 6.2 ppm (q) of vinyl, 6.0 ppm (d) of vinyl, 5.0 ppm (m, broad) of CH$_2$ of glycolate unit, 4.4–4.6 ppm (m, broad) includes CH$_2$ groups of HEA and CH$_2$OH of last glycolate segment of macromer.

This degradable cross linker could be attached to the PVA backbone by isocyanate coupling reaction between the hydroxyl groups. A suitable diiisocyanate such as HMDI (hexamethylene diisocyanate) or IPDI (isophorone diisocyanate) can be employed for this reaction.

Example 9

Preparation of Degradable PVA Containing HEMA-Glycolate Cross Linker

Synthesis of HEMA-Glycolate-OH 120 mL of DCM and Et$_3$Al solution in hexane (1 M solution, 28.8 mL, 29 mmol) were placed in a flask that had been flame dried and purged with nitrogen, and equipped with a rubber septum. The contents in the flask were cooled to 0° C. for about 15 minutes. Under vigorous stirring, freshly distilled HEMA (3.5 mL, 29 mmol) in 30 mL of DCM was added by cannula to the flask containing the Et$_3$Al solution. The color of the solution turned yellow on addition of the HEMA and stayed yellow for a few seconds. The contents were stirred at 0° C. for 10 minutes and then at room temperature for 1 h. The flask was then transferred to an oil bath and stirred at 40° C. for an additional 30 minutes. Glycolide (3.4 g, 29 mmol) was quickly weighed out into a clean dry flask with a stir bar and the flask was sealed with a rubber septum. About 120 mL of DCM was cannulated into the flask containing the glycolide and the contents were stirred to effect dissolution. The glycolide solution was then cannulated into the flask containing the HEMA-Et$_3$Al solution at 40° C. The contents of the flask remained clear during this addition but became turbid with progress of the reaction. The contents were allowed to stir for 20 h at room temperature. At the end of the reaction the mixture was cooled to 0°

C. in an ice bath and trifluoroacetic acid (100 mL) was added to the reaction mixture with vigorous stirring until most of the prepolymer dissolved. The mixture was then stirred at room temperature for an additional 10 minutes. On addition of the trifluoroacetic acid, the turbid mixture became increasingly translucent. The mixture was then filtered through a coarse frit funnel and the filtrate was concentrated in a rotary evaporator to remove all solvents (DCM, TFA, Hexane). The product was a yellow liquid. One method of purification is column chromatography using silica gel with DCM:diethyl ether mixture (80:20, v/v) as the eluting solvent mixture. As column chromatography can be time consuming, a differential solubility technique was developed to separate the HEMA-glycolate product from the catalyst byproduct. It should be noted that both purification methods resulted in products that had identical characterization results by TLC and NMR techniques. For the differential solubility purification method, the HEMA-glycolate product (yellow liquid) was added slowly into dichloroethane to precipitate the unwanted byproduct. The HEMA-glycolate product remains in solution and can be separated from the solid byproduct by filtration. The filtrate is then concentrated on a rotary evaporator under reduced pressure. The product is a yellow liquid that is dried in a vacuum oven overnight at room temperature. Carbon NMR and Proton NMR characterization confirm the formation of the product i.e. HEMA attached to 2 glycolate units (from 1 glycolide unit). $^1$H NMR (CDCl$_3$/CF$_3$COOD mixture) 6.3 ppm (d, 1H) of vinyl, 5.8 ppm (d, 1H) of vinyl, 5.0 ppm (m, 2H) of CH$_2$ of glycolate unit, 4.4–4.6 ppm (m, broad, 6H) includes CH$_2$ groups of HEMA and CH$_2$OH of last glycolate segment of oligomer, 2.0 ppm (s, 3H) of CH$_3$ group of HEMA. GPC analysis was done of the starting material (HEMA), the product HEMA-glycolate-OH, and the product spiked with HEMA. Analysis of the plots shows the presence of the product and the absence of the starting material, HEMA. Also, GC–MS analysis was done of the starting material (HEMA), the product HEMA-glycolate-OH, and the product spiked with HEMA. An evaluation of the plots show 3 peaks for the product, which correspond to the major molecular weight fragments (M$^+$ ions) from the HEMA-glycolate-OH product. No peaks corresponding to unreacted HEMA are seen.

This degradable cross linker could be attached to the PVA polymer as described above in Example 8.

Example 10

Insitu Synthesis of HEMA-Glycolate-COOH 70 mL of DCM and Et$_3$Al solution in hexane (1 M solution, 14.5 mL, 14.5 mmol) were placed in a flask that had been flame dried and purged with nitrogen, and equipped with a rubber septum. The contents in the flask were cooled to 0° C. for about 15 minutes. Under vigorous stirring, freshly distilled HEMA (1.75 mL, 14.4 mmol) in 30 mL of DCM was added by cannula to the flask containing the Et$_3$Al solution. The color of the solution turned yellow on addition of the HEA and stayed yellow for a few seconds. The contents were stirred at 0° C. for 15 minutes and then at room temperature for 1 h. The flask was then transferred to an oil bath and stirred at 40° C. for an additional 30 minutes. Glycolide (5.1 g, 43.2 mmol) was quickly weighed out into a clean dry flask with a stir bar and the flask was sealed with a rubber septum. About 125 mL of DCM was cannulated into the flask containing the glycolide and the contents were stirred to effect dissolution. The glycolide solution was then cannulated into the flask containing the HEMA-Et$_3$Al solution at 40° C. Immediately after the cannulation of the glycolide was complete, a solution of succinic anhydride (1.5 g, 14.4 mmol) in 60 mL of DCM was cannulated into the reaction flask. The reaction mixture was homogeneous after the addition of glycolide and succinic anhydride solutions. The mixture was stirred for 15 minutes at 40° C., and then for 20 h at room temperature. At the end of the reaction the mixture was homogeneous and yellow in color. The mixture was cooled to 0° C. in an ice bath, and trifluoroacetic acid (30 mL) was added to the reaction mixture with vigorous stirring. On allowing the reaction mixture to stand, a yellowish white precipitate settled to the bottom of the flask and was removed by filtration through a coarse frit funnel. The precipitation of the filtrate was checked in diethyl ether. The filtrate (about 300 mL) was added in drops to diethyl ether (1200 mL) with rapid stirring to yield a white precipitate. The precipitate was filtered using a frit funnel under aspirator pressure and the product was dried in a vacuum oven overnight at room temperature. Carbon NMR and Proton NMR characterization confirms the formation of the product i.e. HEMA attached to glycolate units that are end-capped with an acid group from the succinic anhydride end capper. $^1$H NMR (CDCl$_3$/CF$_3$COOD mixture) 6.3 ppm (d, 1H) of vinyl, 5.8 ppm (d, 1H) of vinyl, 5.0 ppm (m, 10H) of CH$_2$ of glycolate unit, 4.4–4.6 ppm (m, broad, 6H) includes CH$_2$ groups of HEMA and CH$_2$ of last glycolate segment, 2.8–3.0 ppm (m, 4H) of succinic anhydride end-capper, 2.0 ppm (s, 3H) of CH$_3$ group of HEMA.

This degradable cross linker could be attached to the PVA polymer as described above in Example 8.

Modifications and variations of the present invention will be apparent to those skilled in the art from the foregoing detailed description. All modifications and variations are intended to be encompassed by the following claims. All publications, patents, and patent applications cited herein are hereby incorporated by reference in their entirety.

What is claimed is:

1. A composition for forming a biodegradable hydrogel comprising two components;

wherein the first component comprises a prepolymer having a poly(vinyl alcohol) backbone having at least one hydroxyl group substituted with a pendant chain bearing a first crosslinking group; and the second component comprises a biodegradable region flanked by second and third crosslinking groups; wherein the second crosslinking group can crosslink with the first crosslinking group of the first component, and the third crosslinking group can crosslink with a crosslinking group on the same or a different first component; and wherein the hydrogel formed from crosslinking of the first and second components degrades in vivo.

2. The composition of claim 1 wherein the first and second components crosslink to form a hydrogel that fully degrades in vivo.

3. The composition of claim 1 wherein the first and second components crosslink to form a hydrogel that partially degrades in vivo.

4. The composition of claim 1 wherein at least one hydroxyl group of the poly(vinyl alcohol) is substituted with a modifier.

5. The composition of claim 1 wherein crosslinking of one or more of the first, second, or third crosslinking groups can be initiated by a mechanism selected from the group consisting of thermal initiation, redox initiation, photoinitiation, or a combination thereof.

6. The composition of claim 4, wherein the modifier is selected from the group consisting of modifiers to change the hydrophobicity of the hydrogel, active agents and groups to allow attachment of an active agent, photoinitiators, modifiers to alter adhesiveness of the hydrogel, modifiers to impart thermoresponsiveness to the hydrogel, and additional crosslinking groups.

* * * * *